United States Patent [19]

Zimmerman

[11] Patent Number: 5,610,125
[45] Date of Patent: Mar. 11, 1997

[54] RHEOPECTIC COSMETIC CLEANSER

[75] Inventor: Amy C. Zimmerman, Ansonia, Conn.

[73] Assignee: Chesebrough-Ponds USA Co., Division of Conopco, Inc., Greenwich, Conn.

[21] Appl. No.: 475,150

[22] Filed: Jun. 7, 1995

[51] Int. Cl.$^6$ .................. C11D 17/00; C07C 67/02; A01N 27/00

[52] U.S. Cl. .................. 510/123; 424/70.1; 424/70.19; 424/78.03; 424/489; 536/1.11; 536/4.1; 536/18.6; 536/124; 514/762; 514/846; 514/847; 514/873; 510/124; 510/125

[58] Field of Search .................. 252/174.21, 174.22, 252/174.23, DIG. 14, 125; 554/227; 560/263; 536/18.6, 1.11, 4.1, 124, 126; 424/70.1, 59, 73, 70.19, 489, 78.03, 502; 514/762, 846, 847, 873; 510/124, 123, 125

[56] References Cited

U.S. PATENT DOCUMENTS

| | | | |
|---|---|---|---|
| 4,536,318 | 8/1985 | Cook et al. | 252/174.17 |
| 4,536,319 | 8/1985 | Payne | 252/174.17 |
| 5,192,462 | 3/1993 | Gloor et al. | 252/174.21 |
| 5,312,559 | 5/1994 | Kacher et al. | 252/125 |
| 5,449,763 | 9/1995 | Wulff et al. | 536/18.6 |

Primary Examiner—Terressa Mosley
Attorney, Agent, or Firm—Milton L. Honig

[57] ABSTRACT

A cosmetic composition is provided in the form of a gel exhibiting semi-solid behavior at rest but under slow shear rates fractures ceasing to act as a fluid and becoming a solid. The cosmetic composition achieves this rheology through a combination of an alkyl polyglycoside with a polyether ester.

4 Claims, No Drawings

RHEOPECTIC COSMETIC CLEANSER

BACKGROUND OF THE INVENTION

1. Field of the Invention

The invention concerns a cosmetic composition of unusual rheology, being a semi-solid at rest while under the slow shear rates of pouring fractures into solid segments.

2. The Related Art

Properly formulated cleansers will effectively and efficiently remove previously applied face powder, rouge, foundation bases, eyeshadow and lipstick. Commercial facial cleansers depend on surfactant ingredients. These surfactants, when contacted with water, sometimes generate a bubbly foam. The cleansers of commerce are usually found in either a gel, lotion or cream form. There is, however, a continual search for less traditional forms that would provide an aesthetically pleasing presentation.

Efforts by this laboratory in seeking less traditional product forms have been focused upon evaluating cooperative properties between various surfactants and thickeners. Among the more interesting surfactants are alkyl polyglycosides which recently have become commercially available. These materials are described in U.S. Pat. No. 4,536,318 (Cook et al.) and U.S. Pat. No. 4,536,319 (Payne). Alkyl polyglycosides are low molecular weight sugars, such as glucose polymerized to a chain length between 1.2 and 3 monomer units, that have been reacted with a $C_8$–$C_{18}$ fatty alcohol. Good foam and exceptional skin mildness are noteworthy properties of these materials.

A wide variety of thickeners are available to the cosmetic chemist. A relatively new entry in this category is reported in U.S. Pat. No. 5,192,462 (Gloor et al.). Therein is described polyether esters formed from the alkoxylation of pentaerythritol. This class of thickening agent is reported to have low reactivity with other chemicals, to have low toxicity and is said to be useful over a broad pH range.

Accordingly, it is an object of the present invention to provide a less traditional product form having an aesthetically pleasing presentation.

It is another object of the present invention to provide a clear gel that opacifies upon being rubbed into the skin.

Still another object of the present invention to provide a cleanser of exceptional foaming and cleaning activity.

These and other objects of the present invention will become more readily apparent from the description and examples which follow.

SUMMARY OF THE INVENTION

In an effort to provide a new format for delivery of a skin cleanser, a variety of surfactants and thickeners, including those mentioned above were evaluated. There has been found through this effort a combination of substances that yields the unexpected rheology of a rheopectic fluid; a fluid for which the structure builds up on shearing, the reverse of thixotropy. The gel of the present invention behaves as a semi-solid at rest, but at slow shear rates, pours from its container as an unstructured liquid. When a given shear rate is exceeded, i.e. by pouring or extrusion through a restricted orifice, the gel fractures ceasing to act as a fluid and becoming a solid. This effect is reversible. Once the solid, or fractured segments, are allowed to stand, all the characteristics of the original semi-solid gel return, i.e. the gel will pour or fracture again depending on the amount of applied force. Other gels of related chemical composition do not exhibit this tendancy to become a solid with increasing shear stress.

More specifically, a cosmetic product is provided that includes:

(i) from about 0.1 to about 40% of an alkyl polyglycoside surfactant having the formula $RO(R^1O)_t(Z)_x$ where Z is a moiety derived from a reducing saccharide containing from 5 to 6 carbon atoms and wherein R contains from about 8 to about 18 carbon atoms and is selected from the group consisting of alkyl, alkylphenyl, hydroxyalkylphenyl, hydroxyalkyl and mixtures thereof; $R^1$ contains from 2 to about 4 carbon atoms; t is from 0 to about 30; and x is a number from about 1.0 to about 10; and (ii) from about 0.1 to about 20% of a polyether ester of the formula:

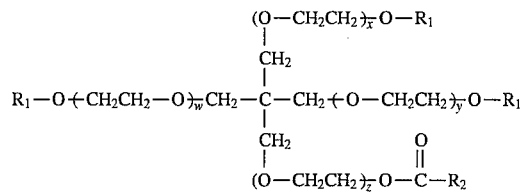

wherein:

$R_1$ is —H or

$R_2$ is a hydrocarbon chain having greater than 5 carbon atoms; and (W+X+Y+Z) is greater than 60.

DETAILED DESCRIPTION OF THE INVENTION

Cosmetic compositions of the present invention will include two essential components. These are an alkyl polyglycoside surfactant and a polyether ester. In combination, these components provide a gel exhibiting the tendancy to become a solid with increasing shear stress.

Alkyl polyglycosides of the present invention are those having a hydrophobic group containing from about 8 to about 20 carbon atoms, preferably from about 10 to about 16 carbon atoms, most preferably from 12 to 14 carbon atoms, and a polysaccharide hydrophilic group containing from about 1.0 to about 10, preferably from 1.3 to 4, most preferably from 1.5 to 2.7 saccharide units (e.g., galactoside, glucoside, fructoside, glucosyl, fructosyl and/or galactosyl units). Mixtures of saccharide moieties may be used in the alkyl polyglycoside surfactants. The number x indicates the number of saccharide units in a particular alkyl polyglycoside surfactant. For a particular molecule, x can only assume integral values. In any physical sample of alkyl polyglycoside surfactant there will in general be molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactosides, fructosides, etc., is preferred. In the preferred product the additional saccharide units are predominately attached to the previous saccharide unit's 2-position. Attachment through the 3-, 4-, and 6-positions can also occur.

Optionally and less desirably there can be a polyalkoxide chain joining the hydrophobic moiety (R) and the polysaccharide-chain. The preferred alkoxide moiety is ethoxide.

Typical hydrophobic groups include alkyl groups, either saturated or unsaturated, branched or unbranched containing from about 8 to about 20, preferably from about 10 to about 16 carbon atoms. Preferably, the alkyl group is a straight chain saturated alkyl group. The alkyl group can contain up to 3 hydroxy groups and/or the polyalkoxide chain can contain up to about 30, preferably less than 10, most preferably 0, alkoxide moieties.

Alkyl polyglycosides are commercially available from the Henkel Corporation of Ambler, Pa., under the trademark Plantareen. For instance, Plantareen 2000 is essentially a $C_8$–$C_{16}$ alcohol reacted polysaccharide with a CTFA designation of Decyl Polyglucose. Also commercially available are the $C_{12}$–$C_{16}$ alcohol derivatives sold under the trademarks Plantareen 1300 and Plantareen 1200.

Amounts of the alkyl polyglycoside may range from about 0.1 to about 40%, preferably from about 1 to about 10%, optimally between about 2 and about 8% by weight.

Polyether esters are the second critical components of compositions according to the present invention. The polyether ester will have the formula:

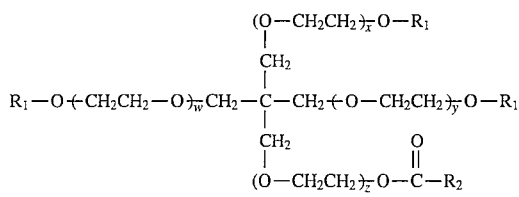

wherein:

$R_1$ is —H or

The hydrocarbon chain may be either straight or branched, having 0 to 6 double bonds, and preferably having 6 to 26 carbon atoms. More preferably, the preferred range of the hydrocarbon chain is from about 12 to 22 carbon atoms, and most preferably 18 carbon atoms. The preferred range for the term (W+X+Y+Z) is in the range from about 100 to 175, and most preferably 150.

Representative polyether esters include: PEG 105 pentaerythritol dibehenate, PEG 105 pentaerythritol tetrabehenate, PEG 150 pentaerythritol tetrastearate, PEG 150 pentaerythritol tetralaurate, PEG 150 pentaerythritol tetraisostearate, PEG 130 pentaerythritol tetrastearate and PEG 75 pentaerythritol tetrastearate. Also contemplated as particularly useful polyether esters in accordance with the present invention are PEG 105 pentaerythritol monobehenate, PEG 105 pentaerythritol tribehenate, PEG 150 pentaerythritol dilaurate, PEG 150 pentaerythritol trilaurate, PEG 150 pentaerythritol monoisostearate, PEG 150 pentaerythritol diisostearate, PEG 150 1pentaerythritol triisostearate, PEG 130 pentaerythritol monostearate, PEG 130 pentaerythritol distearate, PEG 130 pentaerythritol tristearate, PEG 75 pentaerythritol monostearate, PEG 75 pentaerythritol distearate, and PEG 75 pentaerythritol tristearate.

Polyether esters are commercially available from Croda, Inc., New York, N.Y., under the trademark Crothix.

Amounts of polyether ester will range from about 0.1 to about 20%, preferably from about 0.5 to about 5%, more preferably from about 1 to about 3% by weight.

Compositions of the present invention advantageously have the alkyl polyglycoside and polyether ester available in a weight ratio of 5:1 to 1:5, preferably from 4:1 to 1:1, optimally from 3:1 to 1.5:1.

Surfactants other than alkyl polyglycosides may also be present in the cosmetic compositions of the present invention. Total concentration of the additional surfactants will range from about 0.5 to about 60%, preferably from about 15 to about 50%, optimally from about 20 to about 35% by weight of the total composition. The surfactant may be selected from the group consisting of anionic, cationic, nonionic and amphoteric actives. Especially useful is the combination of an anionic and an amphoteric surfactant to complement the alkyl polyglycoside, which is a nonionic surfactant.

Most advantageously, compositions of the present invention will contain an anionic surfactant from the class known as $C_{10}$–$C_{20}$ acyl isethionate. Sodium cocoyl isethionate, available commercially as Tauranol AC 78 E, is most preferred. Amounts of the acyl isethionate will range from about 0.5 to about 20%, preferably from about 1 to about 10%, optimally from about 3 to about 6% by weight.

Further useful anionic surfactants are the $C_8$–$C_{20}$ alkyl ether sulfates with alkoxylation ranging from about 1 to about 100 moles per hydrophobe group, most especially about 2 moles ethylene oxide. Preferred is sodium laureth sulfate available commercially as Standamul ES-2. Amounts of the alkyl ether sulfate will range from about 1 to about 30%, preferably from about 5 to about 20% optimally between about 10 and 18% by weight.

Still further anionic surfactants which may be included in compositions of this invention are: alkyl sulfates, alkylbenzene sulfonates, alkyl glyceryl ether sulphates, dialkyl sulfosuccinates, olefin sulfonates, soap and combinations thereof.

Among the useful nonionic surfactants are the alkoxylated fatty alcohols and fatty acids, but most especially saccharide fatty amides such as the methyl gluconamides.

Advantageously, an amphoteric surfactant may be included in compositions of the present invention. Most suitable are the $C_1$–$C_{30}$ alkyl amidopropyl betaines, e.g. wheat germamidopropyl betaine commercially available as Schercotaine WOAB.

Amounts of the betaine may range from about 0.1 to about 20%, preferably from about 1 to about 10%, optimally between about 3 and 8% by weight.

Compositions of the present invention will contain water in amounts which may range from about 5 to about 90%, preferably from about 30 to about 75%, optimally from about 45 to about 60% by weight.

Humectants of the polyhydric alcohol-type may also be included in the compositions of this invention. The humectant aids in reducing scaling, stimulates removal of built-up scale and improves skin feel. Typical polyhydric alcohols include glycerol (glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from about 0.5 to about 30%, preferably between 1 and 15% by weight of the composition.

Emollient materials in the form of silicone oils and synthetic esters may be incorporated into compositions of the present invention. Amounts of the emollients may range anywhere from about 0.1 to about 30%, preferably between about 1 to about 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkyl and alkenyl esters of fatty acids having 10 to 20 carbon atoms. Examples thereof include myristyl myristate, isopropyl myristate, isononyl isononanoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, imidazolidinyl urea, sodium dehydroxyacetate, propyl paraben benzyl alcohol and iodopropynyl butyl carbamate (known by its CTFA designation of DMDM Hydantoin and commercially available as Glydant Plus). The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be included in the cosmetic compositions. These ingredients include sequesterants (such as disodium EDTA), vitamins (such as Vitamin E, acetate, Vitamin A palmitate and DL-panthenol) and fragrances.

Compositions of the present invention are preferably gels that are transparent or at least translucent. Products based on the present invention may be useful as hand lotions, foot care formulas, shampoos, sunscreens, foam baths and the like.

The following Examples will more fully illustrate the embodiments of this invention. All parts, percentages and proportions referred to herein and in the appended claims are by weight unless otherwise indicated.

EXAMPLE 1

A gel according to the present invention was prepared having the following formula:

| COMPONENT | WEIGHT % |
| --- | --- |
| Sodium Laureth Sulfate | 15.00 |
| Glycerin | 10.00 |
| Wheat Germamidopropyl Betaine | 6.00 |
| Decyl Polyglucose | 6.00 |
| Sodium Cocoyl Isethionate | 5.50 |
| Crothix ® (Polyether Ester) | 2.00 |
| Fragrance | 0.25 |
| DMDM Hydantoin | 0.10 |
| Disodium EDTA | 0.05 |
| Water | qs |

EXAMPLE 2

Several formulations were prepared to evaluate the relative effect of alkyl polyglycoside and polyether ester on rheological properties. Table I lists the evaluated formulations.

TABLE I

| | FORMULATION (WEIGHT %) | | | | |
| --- | --- | --- | --- | --- | --- |
| INGREDIENT | A | B | C | D | E |
| Glycerin | 10.00 | 10.00 | 10.00 | 10.00 | 10.00 |
| Sodium Laureth Sulfate | 15.00 | 15.00 | 15.00 | 18.00 | 0.00 |
| Decyl Polyglucose | 6.00 | 6.00 | 6.00 | 6.00 | 6.00 |
| Wheat Germ-amidopropyl Betaine | 6.00 | 6.00 | 6.00 | 6.00 | 6.00 |
| Sodium Cocoyl Isethionate | 5.50 | 5.50 | 5.50 | 5.50 | 5.50 |
| Crothix ® (Polyether Ester) | 1.00 | 2.00 | 3.00 | 2.00 | 2.00 |
| DMDM Hydantoin | 0.10 | 0.10 | 0.10 | 0.10 | 0.10 |
| Disodium EDTA | 0.05 | 0.05 | 0.05 | 0.05 | 0.05 |
| Water | to 100 | to 100 | to 100 | to 100 | to 100 |

Viscosity measurements were taken on each of the formulations using a Haake Viscometer. Formulations B, C and D all exhibited fracturing, with Formulation C having the most structure, followed by Formulation D and then Formulation B. Formulations A and E did not exhibit any fracturing. Formulation A was sheer thinning, pseudoplastic. Formulation E was classic Newtonian in its flow characteristics.

Although this invention has been described with reference to specific Examples, it will be apparent to one skilled in the art that various modifications will be suggested, all of which are within the spirit and purview of this invention.

What is claimed is:

1. A cosmetic composition comprising:
   (i) from about 0.1 to about 40% of an alkyl polyglycoside surfactant having the formula $RO(R^1O)_t(Z)_x$ where Z is a moiety derived from a reducing saccharide containing from 5 to 6 carbon atoms and wherein R contains from about 8 to about 18 carbon atoms and is selected from the group consisting of alkyl, alkylphenyl, hydroxyalkylphenyl, hydroxyalkyl and mixtures thereof; $R^1$ contains from 2 to about 4 carbon atoms; t is from 0 to about 30; and x is a number from about 1.0 to about 10; and
   (ii) from about 0.1 to about 20% of a polyether ester of the formula:

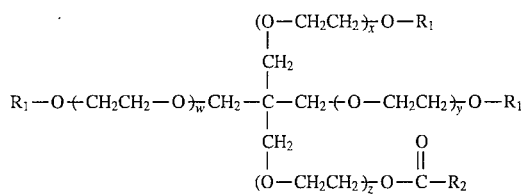

wherein:

$R_1$ is —H or

$R_2$ is a hydrocarbon chain having greater than 5 carbon atoms; and (W+X+Y+Z) is greater than 60, and wherein the composition is a semi-solid gel at rest which upon application of slow shear converts to a solid.

2. A cosmetic composition according to claim 1, further comprising from about 0.5 to about 20% by weight of a $C_{10}$–$C_{20}$ acyl isethionate.

3. A cosmetic composition according to claim 2, further comprising from about 0.1 to about 20% by weight of an alkyl amidopropyl betaine.

4. A cosmetic composition according to claim 2, further comprising from about 1 to about 30% by weight of an alkyl ether sulfate.

* * * * *